US012598374B2

(12) United States Patent
Lacroix et al.

(10) Patent No.: US 12,598,374 B2
(45) Date of Patent: Apr. 7, 2026

(54) TECHNIQUES FOR MINIMIZING POWER CONSUMPTION IN PHOTODETECTOR MEASUREMENTS

(71) Applicant: ActLight SA, Lausanne (CH)

(72) Inventors: Antoine Lacroix, Thonon-les-Bains (FR); Lucas Perrin, Gland (CH); Maxim Gureev, St-Sulpice (CH)

(73) Assignee: ActLight SA, Lausanne (CH)

( * ) Notice: Subject to any disclaimer, the term of this patent is extended or adjusted under 35 U.S.C. 154(b) by 386 days.

(21) Appl. No.: 18/476,194

(22) Filed: Sep. 27, 2023

(65) Prior Publication Data

US 2025/0106504 A1 Mar. 27, 2025

(51) Int. Cl.
*A61B 5/024* (2006.01)
*H04N 23/65* (2023.01)
*H04N 25/709* (2023.01)

(52) U.S. Cl.
CPC ....... *H04N 23/651* (2023.01); *A61B 5/02427* (2013.01); *H04N 25/709* (2023.01)

(58) Field of Classification Search
CPC . A61B 5/0205; A61B 5/1455; A61B 5/14551; A61B 5/14552; A61B 5/02405; A61B 5/02416; A61B 5/02438; A61B 5/1495
See application file for complete search history.

(56) References Cited

U.S. PATENT DOCUMENTS

| | | | |
|---|---|---|---|
| 4,202,000 A | 5/1980 | Carballes | |
| 4,484,210 A | 11/1984 | Shiraki et al. | |
| 4,833,346 A | 5/1989 | Marple | |
| 6,808,957 B1 | 10/2004 | Ho et al. | |
| 9,012,960 B2 | 4/2015 | Okhonin | |
| 9,142,692 B2 | 9/2015 | Sheu | |

(Continued)

FOREIGN PATENT DOCUMENTS

| | | |
|---|---|---|
| CN | 101236995 A | 8/2008 |
| CN | 102460763 A | 5/2012 |

(Continued)

OTHER PUBLICATIONS

Cova et al., "Avalanche Photodiodes and Quenching Circuits for Single-Photon Detection," Applied Optics, Optical Society of America, Washington, DC, US, vol. 35, No. 12, Apr. 20, 1996, pp. 1956-1976 (21 pages).

(Continued)

*Primary Examiner* — Chu Chuan Liu
(74) *Attorney, Agent, or Firm* — Wilmer Cutler Pickering Hale and Dorr LLP

(57) ABSTRACT

Techniques for minimizing power consumption in photodetector measurements are provided. The techniques utilize a method for controlling a photodetector, including the steps of receiving, by a system comprising memory and one or more processors, a target value of the photodetector, receiving, by the system, an output from the photodetector, and processing, by a neural network of the system, the output from the photodetector. The neural network outputs a health signal and, based at least on the health signal and the target value, the system generates a bias signal and applies the bias signal to the photodetector to drive the photodetector to the target value.

20 Claims, 9 Drawing Sheets

400

(56) References Cited

U.S. PATENT DOCUMENTS

| | | | |
|---|---|---|---|
| 9,236,520 B2 | 1/2016 | Okhonin et al. | |
| 9,431,566 B2 | 8/2016 | Okhonin | |
| 9,735,304 B1 | 8/2017 | Okhonin et al. | |
| 10,269,855 B2 | 4/2019 | Sallin et al. | |
| 10,964,837 B2 | 3/2021 | Sallin et al. | |
| 11,114,480 B2 | 9/2021 | Okhonin et al. | |
| 11,183,524 B2 | 11/2021 | Sato | |
| 11,251,217 B2 | 2/2022 | Okhonin et al. | |
| 11,435,446 B2 * | 9/2022 | Hall | G01S 7/497 |
| 11,587,960 B2 | 2/2023 | Okhonin et al. | |
| 2003/0001080 A1 | 1/2003 | Kummaraguntla et al. | |
| 2003/0223053 A1 | 12/2003 | Liu et al. | |
| 2006/0022223 A1 | 2/2006 | Kumesawa | |
| 2006/0039666 A1 | 2/2006 | Knights et al. | |
| 2008/0277701 A1 | 11/2008 | Lee et al. | |
| 2010/0084729 A1 | 4/2010 | Steinbrueck et al. | |
| 2010/0155806 A1 | 6/2010 | Fourches | |
| 2010/0230720 A1 | 9/2010 | Wicks | |
| 2010/0237455 A1 | 9/2010 | Lee | |
| 2010/0271108 A1 | 10/2010 | Sanfilippo et al. | |
| 2011/0024808 A1 | 2/2011 | Janesick | |
| 2011/0133160 A1 | 6/2011 | Yu et al. | |
| 2011/0220969 A1 | 9/2011 | Masuoka et al. | |
| 2011/0272561 A1 | 11/2011 | Sanfilippo et al. | |
| 2011/0292380 A1 | 12/2011 | Bamji | |
| 2012/0056096 A1 | 3/2012 | Abeles et al. | |
| 2012/0313155 A1 | 12/2012 | Okhonin | |
| 2013/0056708 A1 | 3/2013 | Kim | |
| 2013/0323873 A1 | 12/2013 | Elasser et al. | |
| 2014/0159188 A1 | 6/2014 | Maimon | |
| 2014/0319640 A1 | 10/2014 | Major et al. | |
| 2015/0057511 A1 * | 2/2015 | Basu | A61B 5/6826 |
| | | | 600/475 |
| 2015/0221806 A1 | 8/2015 | Okhonin | |
| 2017/0365636 A1 | 12/2017 | Mazzillo et al. | |
| 2018/0175095 A1 | 6/2018 | Sallin et al. | |
| 2018/0247968 A1 | 8/2018 | Na et al. | |
| 2019/0013427 A1 | 1/2019 | Ting et al. | |
| 2019/0067357 A1 | 2/2019 | Cheng et al. | |
| 2019/0239753 A1 * | 8/2019 | Wentz | A61B 5/0075 |
| 2019/0252570 A1 | 8/2019 | Sallin et al. | |
| 2020/0135776 A1 | 4/2020 | Finkelstein | |
| 2020/0185560 A1 | 6/2020 | Giroud-Garampon et al. | |
| 2021/0022676 A1 * | 1/2021 | Lamego | A61B 5/02055 |
| 2022/0087557 A1 * | 3/2022 | Verma | A61B 5/0205 |
| 2023/0228855 A1 | 7/2023 | Perrin et al. | |

FOREIGN PATENT DOCUMENTS

| | | | |
|---|---|---|---|
| CN | 102901992 A | 1/2013 | |
| CN | 105849908 A | 8/2016 | |
| CN | 109155325 A | 1/2019 | |
| CN | 110416335 A | 11/2019 | |
| JP | H05-110056 A | 4/1993 | |
| JP | H07-142761 A | 6/1995 | |
| JP | H07-302928 A | 11/1995 | |
| JP | H08-506456 A | 7/1996 | |
| JP | H09-331051 | 12/1997 | |
| JP | 2003-244074 A | 8/2003 | |
| JP | 2005-235893 A | 9/2005 | |
| JP | 2005-303268 A | 10/2005 | |
| JP | 2005-347599 A | 12/2005 | |
| JP | 2006-210919 | 8/2006 | |
| JP | 2007-526448 A | 9/2007 | |
| JP | 2011-007622 A | 1/2011 | |
| JP | 2013/157619 A | 8/2013 | |
| JP | 2016-066766 | 4/2016 | |
| JP | 2018-088488 | 6/2018 | |
| JP | 2018-190797 | 11/2018 | |
| TW | 446196 U | 7/2001 | |
| WO | WO-2004/114369 A2 | 12/2004 | |
| WO | WO-2005/078801 | 8/2005 | |
| WO | WO-2013/124956 A1 | 8/2013 | |
| WO | WO-2014/021115 | 2/2014 | |
| WO | WO-2018/160721 A1 | 9/2018 | |
| WO | WO-2022/208167 A1 | 10/2022 | |

OTHER PUBLICATIONS

Fossum et al., "A Review of the Pinned Photodiode for CCD and CMOS Image Sensors," IEEE Journal of the Electron Devices Society, vol. 2, No. 3, pp. 33-43, May 2014.

Klein et al., "Design and Performance of Semiconductor Detectors With Integrated Amplification and Charge Storage Capability," Nuclear Instruments and Methods in Physics Research. Section A: Accelerators, Spectrometers, Detectors, and Associated Equipment, Elsevier BV, vol. A305, Aug. 1, 1991, pp. 517-526 (10 pages).

Notice of Reasons for Rejection received in Japanese Patent Application No. 2016-547246. 6 pages.

Notification of International Search Report and Written Opinion dated Aug. 5, 2022 in related PCT/IB2022/000164 filed Mar. 29, 2022 (11 pages).

Notification of International Search Report and Written Opinion dated Jun. 28, 2018 in related PCT/IB2018/000356 filed Mar. 16, 2018 (19 pages).

Raissi, "A brief analysis of the field effect diode and breakdown transistor," IEEE Transactions on Electron Devices, Feb. 1996, vol. 43, Issue 2, pp. 362-365 (4 pages).

Sallin et al., "MOS-PN Hybrid Device With Minimum Dark Current for Sensitive Digital Photdection," IEEE Photonics Technology Letters, IEEE Service Center, vol. 26, No. 20, Oct. 15, 2014, pp. 2062-2065.

Salman et al., "Field Effect Diode (FED): A Novel Device for ESD protection in deep sub-micron SOI technologies," International Electron Devices Meeting, Dec. 11-13, 2006, IEEE. 4 pages.

Takahashi et al., "A 45 nm Stacked CMOS Image Sensor Process Technology for Submicron Pixel," Sensors, Dec. 5, 2017, vol. 17:2816, 13 pages.

Van Nieuwenhove et al., "Photonic Demodulator With Sensitivity Control," IEEE Sensors Journal, IEEE Service Center, vol. 7, No. 3, Mar. 1, 2007, pp. 317-318 (2 pages).

* cited by examiner

100

302

400

500

Light

Target Value
LED Power

Neural
Network 502

Photodetector
504

Output

Health Data
Extractor
506

700

PPG signal
702

TECHNIQUES FOR MINIMIZING POWER CONSUMPTION IN PHOTODETECTOR MEASUREMENTS

CROSS-REFERENCE TO RELATED APPLICATIONS

This patent application incorporates by reference U.S. Pat. No. 10,964,837 (the '837 patent), entitled "Photo detector systems and methods of operating same," filed Apr. 17, 2019, U.S. Pat. No. 11,587,960 (the '960 patent), entitled "Photodetector," filed on Nov. 20, 2020, and U.S. patent application Ser. No. 17/580,052, entitled "Control Techniques for Photodetector Systems," filed Jan. 20, 2022 (the '052 application).

FIELD OF THE DISCLOSURE

The present disclosure relates generally to photodetectors and, more particularly, to techniques for minimizing power consumption in photodetector measurements.

BACKGROUND OF THE DISCLOSURE

A traditional photodetector may be operated by being held at a constant reverse bias voltage. Incident photons are absorbed in a light absorbing region of the photodetector to generate electron-hole pairs, which gravitate toward electrical contacts of the photodetector. The magnitude of the generated photocurrent is proportional to the intensity of the light incident on the photodetector. With traditional photodetectors having a constant bias voltage, there is little, if any, room for fine tuning or adjustment to optimize power consumption and/or performance. To make matters worse, traditional photodetectors are often used with an amplifier to amplify the very weak signal they produce. An unwanted consequence of such an amplifier is the introduction of noise into the signals acquired from the photodetector, as well as being another drain on precious power resources.

The field of health data acquisition and health data processing presents particular challenges with the use of photodetectors to acquire biological signals. For example, a wrist-worn heart rate monitor may use a traditional photodetector as described above to record light that is received after being transmitted into the wearer's skin and reflected off biological structures in the wearer's body (e.g., blood vessels) for generating a health data signal to interpret. However, there are numerous internal and external factors that may yield a non-existent or a low-quality health data signal. Internal factors such as an amount of power supplied to light sources to generate the transmitted light may be too low to generate a sufficient signal or too high so as to cause additional and unnecessary power to be drained. External factors such as ambient lighting conditions or motion of the photodetector relative to the wearer (e.g., moving around the wrist, being removed entirely) can cause the health data signal to be unusable or unreliable. Other applications, such as tracking of SPO2 levels and time-of-flight (ToF) measurements where conditions vary greatly (e.g., the automotive industry, facial recognition), may encounter similar and/or additional problems.

To address and/or rectify the above-described problems, it would be useful to provide a control scheme that intelligently adjusts a photodetector to be as sensitive as it needs to be to acquire a sufficiently useful signal in the presence of internal and/or external factors that could negatively impact performance if not properly accounted for, while simultaneously minimizing power consumption and avoiding any additional noise from electronic components that are used to boost the signal.

In view of the foregoing, it should be understood that there are significant problems and shortcomings associated with current photodetector technologies.

SUMMARY OF THE DISCLOSURE

Techniques for minimizing power consumption in photodetector measurements are disclosed. In one particular embodiment, the techniques may be realized as a method for controlling a photodetector, the method including the steps of receiving, by a system comprising memory and one or more processors, a target value of the photodetector, receiving, by the system, an output from the photodetector, and processing, by a neural network of the system, the output from the photodetector. The method includes outputting, by the neural network, a health signal, generating, by the system and based at least on the health signal and the target value, a bias signal, and applying, by the system, the bias signal to the photodetector to drive the photodetector to the target value.

In accordance with other aspects of this particular embodiment, the method includes providing, by the system, the health signal to a photoplethysmography algorithm implemented by the system. Additionally, the photoplethysmography algorithm includes determining from the health signal, a delay between a first candidate heartbeat and a second candidate heartbeat and determining, a signal quality of the first candidate heartbeat and the second candidate heartbeat.

In accordance with other aspects of this particular embodiment, determining the signal quality of the first candidate heartbeat and the second candidate heartbeat includes determining that the health signal includes a false positive responsive to determining that a delay between the first candidate heartbeat and the second candidate heartbeat is lower than a first threshold amount of time and/or determining that the health signal is unreliable responsive to determining that a delay between the first candidate heartbeat and the second candidate heartbeat is higher than a second threshold amount of time.

In accordance with further aspects of this particular embodiment, the photoplethysmography algorithm further includes computing an inter-beat interval between the first candidate heartbeat and the second candidate heartbeat.

In accordance with additional aspects of this particular embodiment, the photoplethysmography algorithm further includes computing heart rate variability based on the inter-beat interval.

In accordance with other aspects of this particular embodiment, computing heart rate variability includes computing a distribution of inter-beat intervals, including the inter-beat interval and computing the heart rate variability as a standard deviation of the distribution of inter-beat intervals.

In accordance with further aspects of this particular embodiment, the method includes receiving, by a digital signal processor of the system, data from one or more sensors, providing, by the digital signal processor, a first signal to the neural network based on the data from the one or more sensors, and providing, by the digital signal processor, a second signal to the photoplethysmography algorithm based on the data from the one or more sensors. Additionally, the photoplethysmography algorithm determines the signal quality of the first candidate heartbeat and the second candidate heartbeat based on the health signal and the second signal.

In accordance with other aspects of this particular embodiment, the method includes determining, by the system, a reliability signal indicating a heartbeat peak is unreliable, determining, by the neural network, a timing of the heartbeat peak, and providing, by the system, the reliability signal and the timing to a photodiode control algorithm implemented by the system. Additionally, the photodiode control algorithm includes modifying the bias signal based on the reliability signal, the timing, and the target value.

In accordance with further aspects of this particular embodiment, the bias signal is a bias voltage, and the photodiode control algorithm further includes increasing the bias voltage responsive to determining the output from the photodetector has a signal quality below the target value and/or lowering the bias voltage responsive to determining the output from the photodetector has a signal quality at or above the target value.

In accordance with other aspects of this particular embodiment, the neural network is trained to recognize, during a time frame, a presence of a heartbeat peak or an absence of a heartbeat peak.

In accordance with additional aspects of this particular embodiment, the method further includes training the neural network, the neural network including an input layer, a hidden layer, and an output layer. The input layer includes a plurality of parameters, the plurality of parameters including one or more of LED power, bias voltage, reflected power, background light, user data, data from an accelerometer, data from a gyroscope, and noise. The output layer includes a node that corresponds to a detected heartbeat for a first logical value and corresponds to an absence of a detected heartbeat for a second logical value.

In accordance with further aspects of this particular embodiment, the output layer only includes the node.

In another particular embodiment, the techniques may be realized as a system for controlling a photodetector, the system including one or more processors and at least one memory, coupled to the one or more processors. The system is configured to provide the one or more processors with instructions that, when executed by the one or more processors, cause the system to receive a target value of the photodetector, receive an output from the photodetector, process, by a neural network of the system, the output from the photodetector, output, by the neural network, a health signal, generate, based at least on the health signal and the target value, a bias signal, and apply the bias signal to the photodetector to drive the photodetector to the target value.

In another particular embodiment, the techniques may be realized as one or more non-transitory computer-readable media storing executable instructions that, when executed by one or more processors, cause a system to control a photodetector by receiving a target value of the photodetector, receiving an output from the photodetector, processing, by a neural network of the system, the output from the photodetector, outputting, by the neural network, a health signal, generating, based at least on the health signal and the target value, a bias signal, and applying the bias signal to the photodetector to drive the photodetector to the target value.

In another particular embodiment, the techniques may be realized as at least one processor readable storage medium storing a computer program of instructions configured to be readable by at least one processor for instructing the at least one processor to execute a computer process for performing the method as recited above.

In another particular embodiment, the techniques may be realized as a system for controlling a photodetector, the system including one or more processors communicatively coupled to a network, wherein the one or more processors are configured to perform the method as recited above.

In another particular embodiment, the techniques may be realized as an article of manufacture for controlling a photodetector, the article of manufacture including at least one processor readable storage medium and instructions stored on the at least one medium, wherein the instructions are configured to be readable from the at least one medium by at least one processor and thereby cause the at least one processor to operate so as to perform the method as recited above.

In another particular embodiment, the techniques may be realized as a system for controlling a photodetector, the system including one or more processors and at least one memory, coupled to the one or more processors. The system is configured to provide the one or more processors with instructions that, when executed by the one or more processors, cause the system to perform the method as recited above.

In another particular embodiment, the techniques may be realized as one or more non-transitory computer-readable media storing executable instructions that, when executed by one or more processors, cause a system to perform the method as recited above.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DETAILED DESCRIPTION OF EMBODIMENTS

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

When a photodetector is activated at a bias voltage $V_{bias}$, there is an inverse relationship between triggering time and absorbed light power, wherein triggering time may be used as the measure of the intensity of the incident light. The triggering time is the time it takes to accumulate a number $N_{tot}$ of electrons in the body region of the photodetector that is needed to trigger the current flow. On the other hand, for a fixed incident light intensity, changing the bias voltage $V_{bias}$ changes the number $N_{tot}$ of electrons needed to trigger the photocurrent in a photodetector. Increasing the bias voltage $V_{bias}$ decreases the number $N_{tot}$ of electrons, while decreasing the bias voltage $V_{bias}$ increases the number $N_{tot}$ of electrons. In an example of the relationship between the number $N_{tot}$ of electrons needed to trigger the photocurrent in a photodetector and the bias voltage $V_{bias}$ in a ToF application, values of $[N_{tot}, V_{bias}]$ are: [22, 1.45V], [15, 1.452V], [5, 1.456V], [2, 1.458V], and [1, 1.46V]. In another example, the value of $N_{tot}$ exponentially increases as $V_{bias}$ linearly decreases. As another example of such values in the context of an application for determining heartrate values, the values are: [3.16×10⁵, 1.7V], [1.26×10⁶, 2V], [7.94×10⁶, 2.5V], [2.00×10⁷, 3V], [3.16×10⁷, 3.3V].

With the understanding that increasing and decreasing the bias voltage $V_{bias}$ respectively decreases and increases (i.e., tunes) the required number $N_{tot}$ of electrons, a control system may be devised to control, tune, adjust, and/or program a parameter (e.g., signal quality) of a photodetector to a target value. For health measurements, $N_{tot}$ can be reduced to lower power consumption, down to a minimum $N_{tot}$, and still give precise results (e.g., reliably detect a heartbeat).

Figure 1:
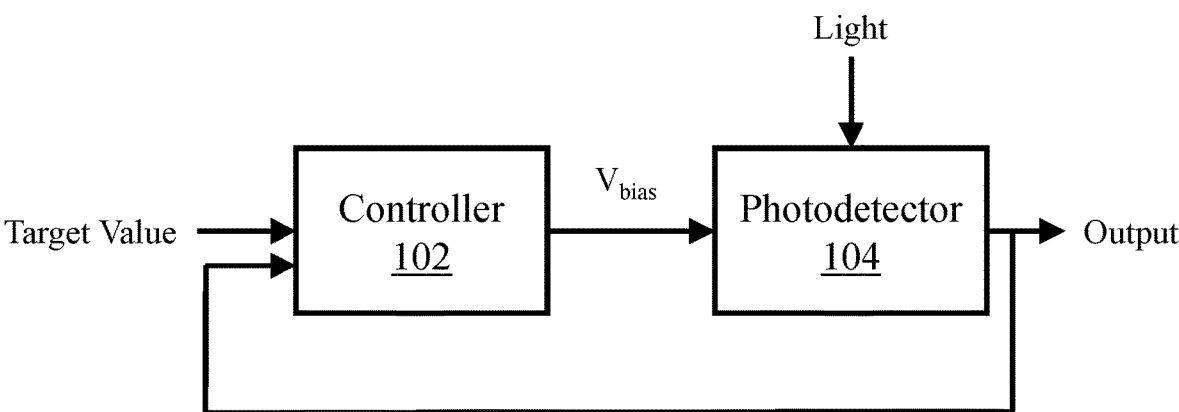
FIG. 1 shows a control system for controlling, tuning, adjusting, and/or programming a parameter corresponding to a photodetector, in accordance with an embodiment of the present disclosure.

FIG. 1 shows a control system 100 for controlling, tuning, adjusting, and/or programming a parameter corresponding to a photodetector. The control system 100 includes a controller 102 and a photodetector 104. The controller 102 may be formed by one or more microcontrollers, processors, or microprocessors. The controller 102 may include one or more memory devices such as dynamic random access memory (DRAM), static random access memory (SRAM), flash memory, a magnetic disk drive, an optical drive, a programmable read only memory (PROM), a read only memory (ROM), or any other memory and combination of memories. The one or more microcontrollers, processors, or microprocessors may implement algorithms, instructions, and/or programs that are stored on the one or more of the memory devices in order to perform the various processes of the present disclosure. The controller 102 may send and receive various signals to and from the photodetector 104.

The controller 102 may receive, as inputs, an output (i.e., Output in FIG. 1) related to a characteristic of the photodetector 104 and a Target Value. The Target Value may be predetermined and set at a fixed value by an operator of the control system 100. Alternatively, the Target Value may be dynamically and/or automatically varied during the operation of the photodetector 104. The Target Value may be the value at which a parameter (e.g., signal quality) of the photodetector 104 may be desired to be set at a given moment in time. The range and type of signal quality can vary greatly. In one case it can be a number of wrongly detected/missed heartbeats per second, which, as an example, should not exceed one wrong heartbeat per 30 seconds, but depends on the application and a required precision. In another example, the Target Value can be the ratio between the amplitude of the PPG peaks and the average signal, in which case a higher ratio means a better signal. The minimum desirable ratio in this case also varies greatly but can be in a range between 5 and 10. This range is one example and other suitable ranges are contemplated.

In some embodiments, the Target Value may be desired independently of the light condition (e.g., light intensity) under which the photodetector 104 operates. The Output may be measured directly from the photodetector 104 or from other parameters of the photodetector 104. Alternatively, the Output may be calculated based on other parameters of the photodetector 104. The Output may be the signal itself output from the photodetector 104 or the Output may be, as described above, as an output related to or derived from the photodetector.

The controller 102 may generate (or compute or formulate) and output and/or apply a bias voltage $V_{bias}$ to the photodetector 104. The bias voltage $V_{bias}$ may forward bias the photodetector 104. Alternatively, the controller 102 may output a bias current to forward bias the photodetector 104, or a bias signal to a driver (not shown) that in turn forward biases the photodetector 104. Based on the Target Value and the Output related to the photodetector 104, the controller 102 may, continuously or at predetermined time intervals, vary the bias voltage $V_{bias}$ (or bias current or bias signal) such that and until the parameter of the photodetector 104 reaches the target value. Examples of parameters of a photodetector that may be controlled, tuned, adjusted, and/or programmed are, but are not limited to, triggering time, signal-to-noise ratio (SNR), light intensity (e.g., LED power), and sampling rate.

Figure 2:
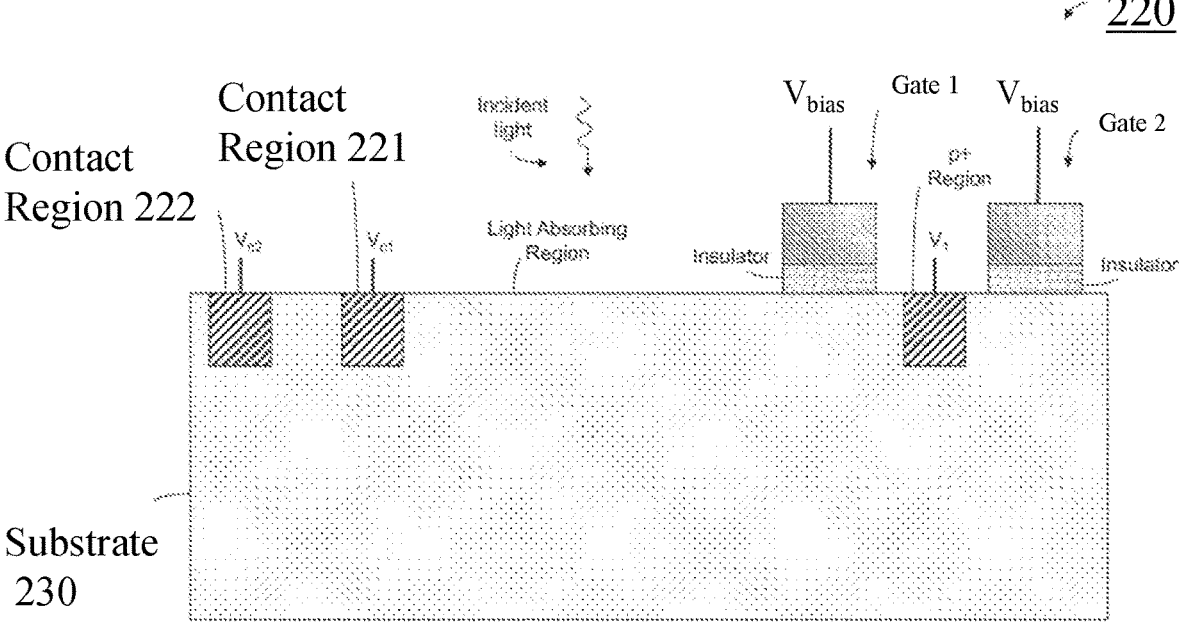
FIG. 2 shows a cross section of a dynamic photodiode, in accordance with an embodiment of the present disclosure.

FIG. 2 shows a cross section of a dynamic photodiode (DPD) 220 that may be employed in conjunction with the present disclosure, wherein the DPD 220 includes a plurality of contact regions disposed on a top side of a substrate 230 (e.g., bulk substrate wafer/die). DPDs of various embodiments include at least one "contact region" (i.e., n+ or p+ type contact regions). The DPD 220, for example, includes a first contact region 221 and a second contact region 222 to improve the performance of the DPD 220 as compared to a detector with a single contact region. In operation, a DC voltage may be applied to the second contact region 222 (e.g., $V_{c2}=0V$, ground) to provide additional control of the potential barriers within the DPD 220 during operation or during the inactive period. Other photo detector embodiments described herein may include more one or more additional contact regions.

The substrate 230 includes a first gate (Gate 1) disposed on the top side of the substrate 230, the first gate configured to receive a voltage, and a second gate (Gate 2) disposed on the top side of the substrate 230, the second gate configured to receive a second voltage. In one embodiment, the first voltage and the second voltage are the bias voltage $V_{bias}$. The DPD 220 includes a doped region disposed on the top side of the substrate 230 between the first gate and the second gate, the doped region being a p+ region. In other embodiments, the doped region is a n+ region.

Acquiring measurements from photodetectors, including DPDs (e.g., the DPD 220), presents many challenges. To acquire any usable signal, there must be enough transmitted light carrying enough energy to reach the photodetector and cause the photodetector to trigger a response. To compound the challenge, power is not in unlimited supply nor is power available at no cost in most circumstances. There is therefore a tradeoff between using enough power to obtain a useable signal and not draining so much power that another measurement cannot be acquired. To make matters more complicated, in the field of portable medical devices, for example, not only is optimal power use desired, but the environment itself may be subject to constant variation. For example, if a photodiode is configured to receive and measure light reflected off human tissue, the optimal parameters for the photodiode may differ between circumstances where internal and/or external conditions have changed. To account for this variation, a neural network is provided and trained specifically to optimize parameters of photodetectors and DPDs described herein.

Figure 3:
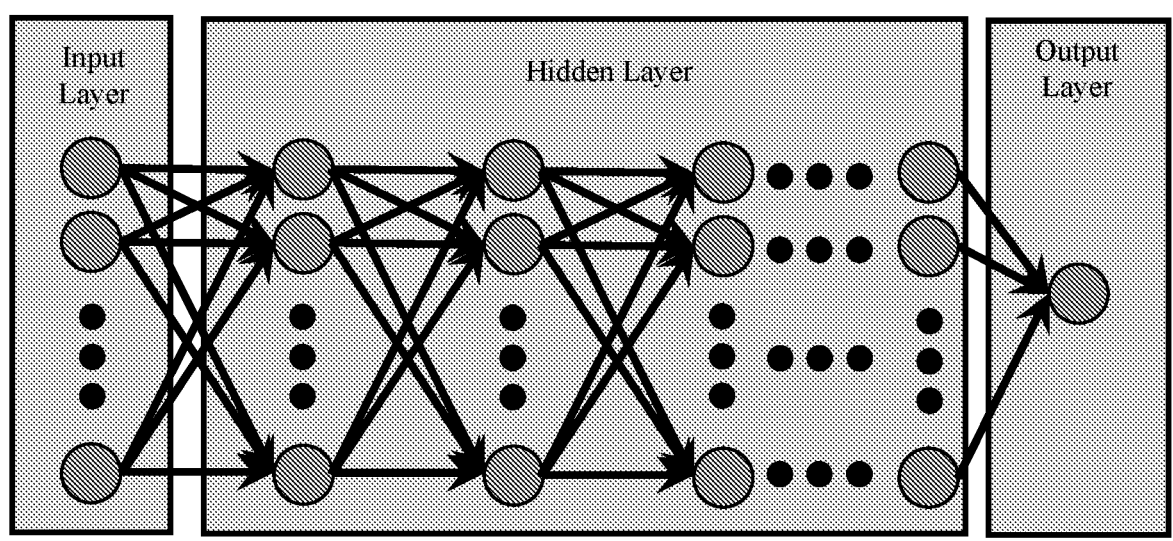
FIG. 3 shows a neural network system, in accordance with an embodiment of the present disclosure.

FIG. 3 illustrates a neural network 302 for use with photodetectors described herein, where the neural network 302 includes an input layer, a hidden layer, and an output layer. The input layer of the neural network 302 receives a plurality of parameters, one parameter for each node in the input layer. Each parameter, in at least one example, is supplied to the neural network 302 by a controller (e.g., the controller 102) of a system (e.g., the system 100). The parameters may include internal parameters and/or external parameters. For example, the internal parameters may include one or more of LED power, a current measurement for the bias voltage $V_{bias}$, and a setting of the photodetector. The external parameters may include one or more of light conditions (e.g., reflected power, background light), user profile data, sensor data (e.g., accelerometer, gyroscope), and noise. The neural network 302 is also provided with the actual PPG signal from the photodetector (e.g., the DPD 220). In some embodiments, the neural network 302 receives the PPG signal directly. In other embodiments, the neural network 302 receives the PPG signal via its derivative and/or normalization.

The hidden layer includes a plurality of weighted neurons that transform the parameters of the input layer into features that are classified in the output layer. The output layer of the neural network 302 includes only one node in the output layer. In one example of the neural network 302, the input layer has 12 neurons (nodes), one hidden layer that is 8 neurons deep, and 1 neuron in the output layer. By constructing a relatively 'small' neural network, the computational efficiency and response time of the applicable controller or processor implanting the neural network improves dramatically. Particularly with health measurements and conditions that can rapidly change from moment to moment (e.g., measuring heart rate using a photodiode near a person's skin), acquiring accurate and frequent measurements while still using minimal power is a challenge. To meet that challenge, in at least one example, the 'small' or 'lightweight' neural network 302 is trained to take input parameters, as described above, and quickly classify the parameters into the single output node: whether there is a heartbeat peak (i.e., a logical '1') or not (i.e., a logical '0'). From this single output, embodiments herein achieve fast and detailed analysis of critical health data. In an example, the number of times the neural network 302 indicates a '1' over a period of time defines a number of heartbeat peaks per that period of time, and therefore defines a heart rate. In addition to the presence or absence of a heartbeat, the neural network 302, as well as other neural networks described herein, in at least one example, is also configured to determine the time/timing or temporal location along a biological signal of the heartbeat's peak.

The output layer of the neural network 302 includes a single neuron/node. Other embodiments of neural networks described herein include more than one neuron/node in their respective outputs. The value of each node or group of multiple nodes is a signal. In the context of health measurements, this signal is a health signal. The health signal, in one example includes the bias voltage $V_{bias}$. In other examples, the health signal includes the detection or absence of the detection of a heartbeat. The health signal is not limited to these examples and in other examples includes any information computed or generated by a neural network. In an example, the health signal may include the exact time of occurrence of a heartbeat peak to supplement the binary '1' or '0' indication of a peak or lack thereof in a particular section or duration of a biological signal.

Figure 4:
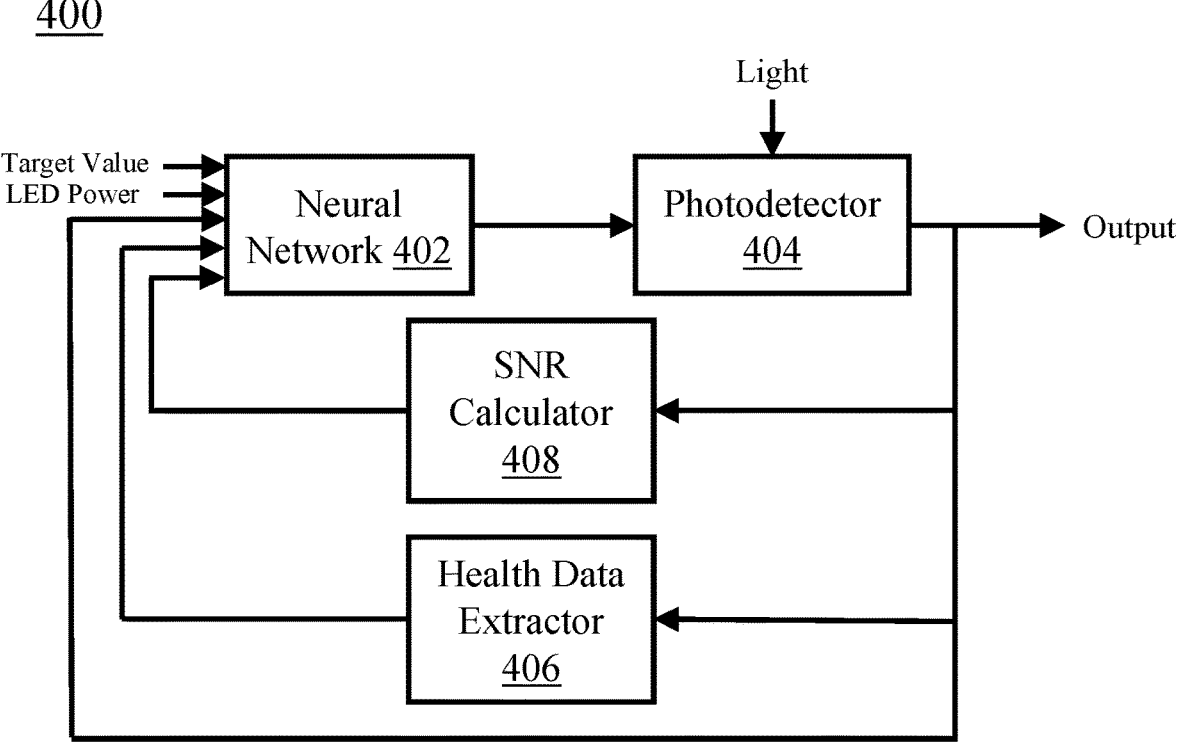
FIG. 4 shows a neural network system for controlling, tuning, adjusting, and/or programming a parameter corresponding to a photodetector, in accordance with an embodiment of the present disclosure.

FIG. 4 illustrates a neural network system 400 for controlling, tuning, adjusting, and/or programming a parameter, the signal-to-noise ratio (SNR), of a photodetector 404 while minimizing power consumption by optimizing the number $N_{tot}$ of electrons needed to generate a photocurrent in the photodetector 404, according to an embodiment of the present disclosure. The neural network system 400 includes a neural network 402, the photodetector 404, a health data extractor 406, and an SNR calculator 408. In one example, the photodetector 404 is identical to the photodetector 104 and the neural network 402 is identical to the neural network 302. In another example, the photodetector 404 is similar to the photodetector 104 and the neural network 402 is similar to the neural network 302.

The neural network 402, health data extractor 406, and SNR calculator 408, each separately or in combination, may be formed by one or more microcontrollers, processors, or microprocessors. The neural network 402, the health data extractor 406, and the SNR calculator 408 may be formed by one or more microcontrollers, processors, or microprocessors. The neural network 402, health data extractor 406, and SNR calculator 408, each separately or in combination, may include one or more memory devices such as DRAM, SRAM, flash memory, a magnetic disk drive, an optical drive, a PROM, a ROM, or any other memory and combination of memories. The one or more microcontrollers, processors, or microprocessors may implement algorithms, instructions, and/or programs that are stored on the one or more of the memory devices in order to perform the various processes of the present disclosure.

Neural networks utilized throughout this disclosure are not limited to only a single output node in the output layer. Depending on the circumstances, for example, it may be beneficial to have additional output layer neurons. In an example, in addition to one output neuron indicating the presence or absence of a heartbeat peak, a second output neuron or group of neurons may be configured to output the bias voltage $V_{bias}$ to control a photodetector. In another example, the neural network directly outputs heart rate and bias voltage, which would use two neurons in the output.

The health data extractor 406 is, in at least one example, configured to extract and/or determine health data in the form of a photoplethysmography (PPG) signal and a heart rate variability (HRV) from the Output of the photodetector 404. In at least one other example, the health data extractor 406 is configured to assess the health data for anomalies including, but not limited to, one or more of wrongly detected heartbeats, missing heartbeats, or rapidly changing heartrate. This health data is used, in certain embodiments, to tune the photodetector 404. The SNR calculator 408 is, in at least one example, configured to extract and/or determine the SNR of the Output. The health data extractor 406 and the SNR calculator 408 may each receive, as input, a measured or calculated triggering time of the photodetector 404 from the Output of the photodetector 404. Based on the triggering time, the SNR calculator 406 may be configured to calculate or compute a value indicative of the SNR of photodetector 404.

The neural network 402 may receive, as inputs, a target SNR (Target Value), the output of the SNR calculator 408, the extracted health data from the health data extractor 406, the measured or calculated triggering time of the photodetector 404, and the power of the light source (LED Power) that emits light that in turn gets reflected and detected by photodetector 404. The Target Value may be predetermined and set at a fixed value by an operator of the neural network system 400. The Target Value may be dynamically and/or automatically varied during the operation of the photodetector 404.

In the field of health data measurements, for example obtaining health data from a person using a portable device (e.g., a DPD worn about a person's wrist), LEDs are utilized to subject a target area of a person to light of one or more particular wavelengths. In one example, the wavelengths are in the infrared region. However, certain embodiments and examples provided and described herein are not limited to LEDs, and instead may be replaced or supplemented with any other suitable light source, such as lasers, to emit light into a person's tissue and obtain a subsequent signal from a DPD.

In certain embodiments, one or more of the neural network 402, the photodetector 404, the health data extractor 406, and the SNR calculator 408 are included in a controller (e.g., the controller 102). Based on the Target Value, the output of the SNR calculator 408, the extracted health data from the health data extractor 406, and the power of the light source, the controller (not shown), including the neural network 402, may generate (or compute or formulate) and output a bias voltage $V_{bias}$ to the photodetector 404. The bias voltage $V_{bias}$ may forward bias photodetector 404. Alternatively, the controller may output a bias current to forward bias the photodetector 404 or a bias signal to a driver (not shown) that in turn forward biases the photodetector 404. Based on the Target Value, LED Power, the Output of the photodetector 404, the output of the health data extractor 406, and the output of the SNR calculator 408, the neural network 402 may, continuously or at predetermined time intervals, vary the bias voltage $V_{bias}$ (or bias current or bias signal) such that the SNR of the photodetector 404 is driven to the Target Value, while minimizing the noise in the extracted health data and power consumed by optimizing the number $N_{tot}$ of electrons needed to generate a photocurrent in the photodetector 404.

While SNR is used as one example of a Target Value, it is to be appreciated that other suitable parameters for the Target Value may be utilized in accordance with the present disclosure. In one example, the Target Value is the ratio of reliable peaks over unreliable peaks obtained in a given time interval. Other suitable Target Values include, but are not limited to, a maximum number of unreliable peaks obtained in a given interval, and the ratio between the amplitude of the PPG peaks and the average signal.

Figure 5:
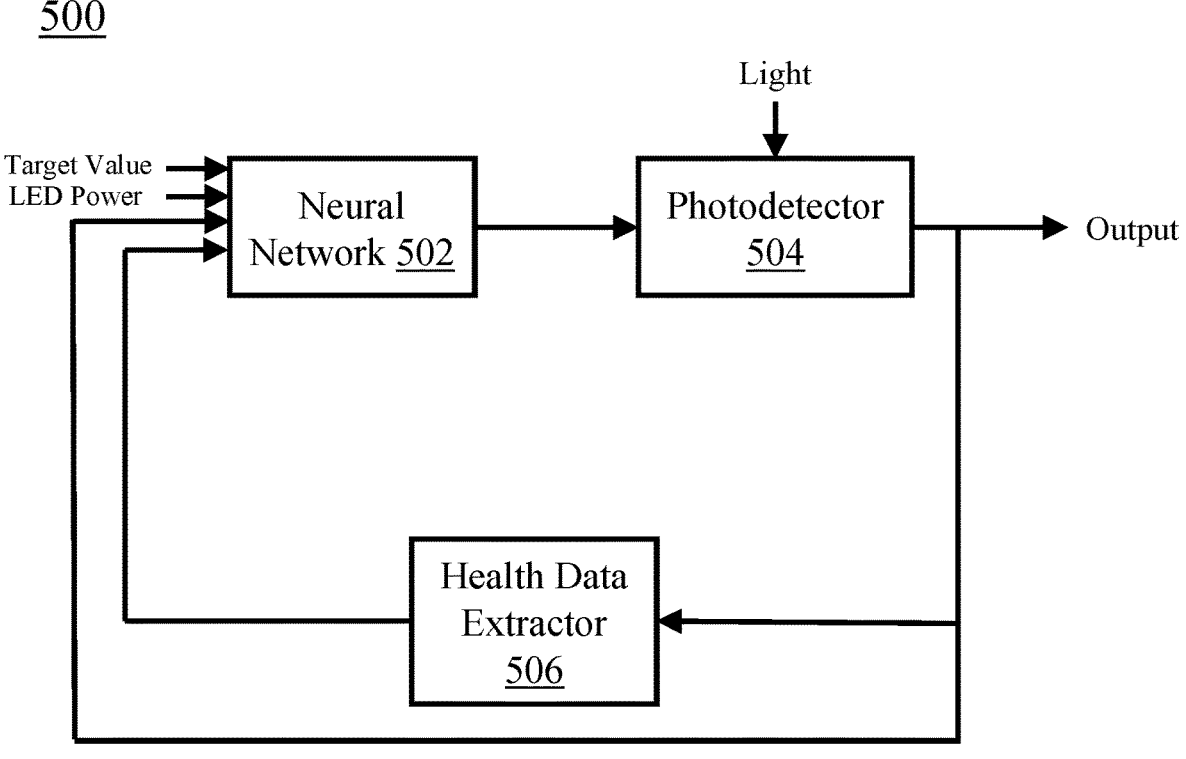
FIG. 5 shows a neural network system for controlling, tuning, adjusting, and/or programming a parameter corresponding to a photodetector, in accordance with an embodiment of the present disclosure.

Signal quality itself may derived using something other than the SNR calculator 408. FIG. 5 illustrates a neural network system 500 which differs from the neural network system 400 in that there is no SNR calculator 408. Instead, a neural network 502 is trained to receive inputs of Target Value, LED Power, the Output of the Photodetector, and the output of a health data extractor 506. The Target Value may be a value for signal quality, and the current quality of the signal in the Output of the photodetector 504 may be determined by the neural network 502 and/or the health data extractor 506. In one example, the Target Value is a fixed number of valid heartbeats in a given period of time and the health data extractor 506 provides a PPG signal to the neural network 502, which outputs a number of heartbeat peaks over the length of the PPG signal, which is then compared to the Target Value by a controller (not shown) including the neural network 502 and the health data extractor 506 to determine whether the bias voltage should increase, decrease, or remain the same. Alternatively, the neural network 502 itself may be configured to have an input that corresponds to a running total of heartbeat peaks that is to be compared to the Target Value. The neural network 502 and the health data extractor 506 may be formed by one or more microcontrollers, processors, or microprocessors. The neural network 502 and the health data extractor 506, each separately or in combination, may include one or more memory devices such as DRAM, SRAM, flash memory, a magnetic disk drive, an optical drive, a PROM, a ROM, or any other memory and combination of memories. The one or more microcontrollers, processors, or microprocessors may implement algorithms, instructions, and/or programs that are stored on the one or more of the memory devices in order to perform the various processes of the present disclosure.

Figure 6A:
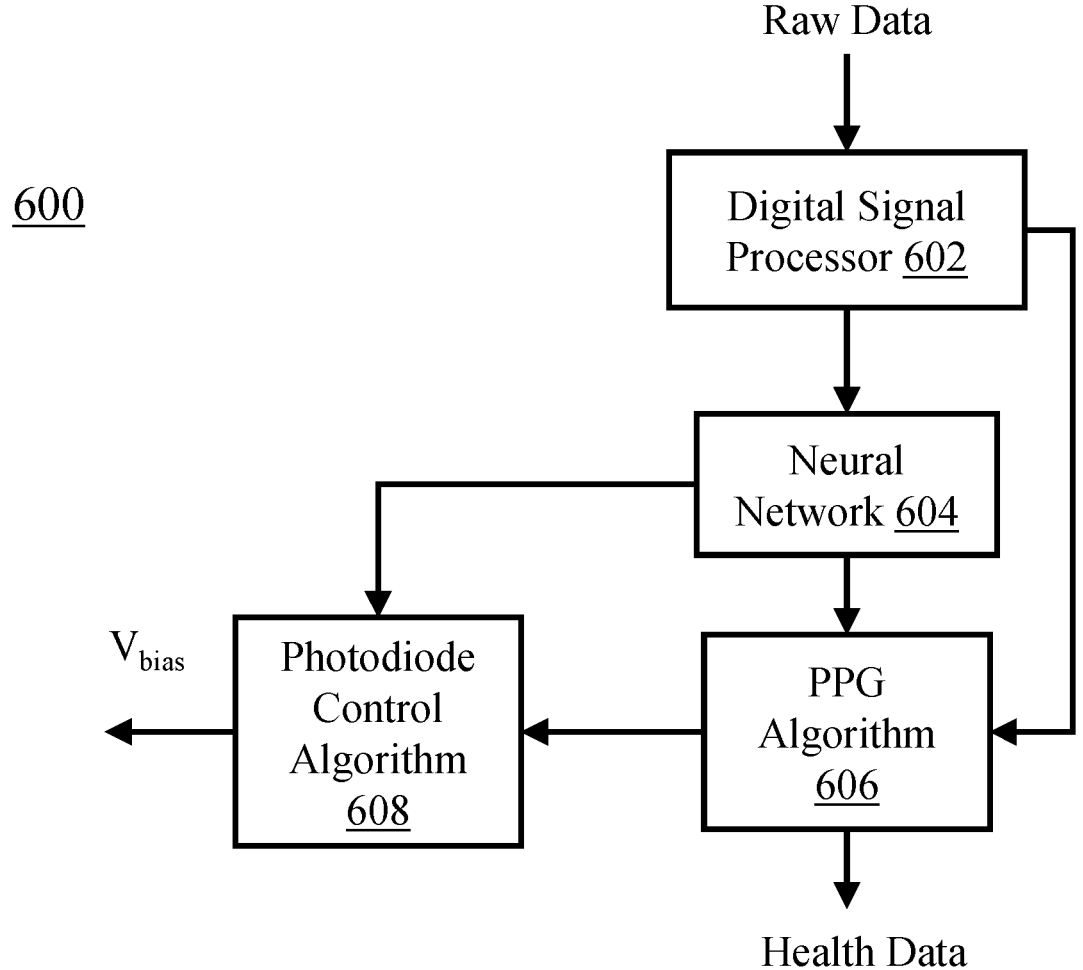
FIG. 6A shows a control process for a neural network system, in accordance with an embodiment of the present disclosure.

FIG. 6A shows a control process 600 for a neural network system. The control process 600 is useable with the control system 100, the neural network system 400, the neural network system 500, and any other suitable photodetector system described herein. The control process 600 may be considered as an AI-based control loop for a DPD as described above. The control process includes a digital signal processor (DSP) 602, which receives Raw Data and provides an output to a neural network 604. The neural network 604 provides its output to both a photodiode control algorithm 608 and a PPG algorithm 606. The PPG algorithm 606 also receives input from the DSP 602 to produce Health Data. The photodiode control algorithm 608 is configured to produce the bias voltage signal $V_{bias}$. The control process 600 may be embodied as a controller, for example, as the controller 102.

The Raw Data is, in at least one example, the signal obtained from one or more sensors of the system, before any filtering or averaging. In one example, the Raw Data is the triggering times of a DPD included in a neural network system as described herein. Other examples incorporate additional sensors if applicable, such as accelerometers and gyroscopes.

The neural network 604 is trained to recognize heartbeats (via their peaks) and give as an output the presence or absence of a heartbeat peak in the considered time frame. This output is given to the PPG algorithm 606, alongside other data from the DSP 602, such as frequency, time, and the signal itself. The DSP 602 provides a first signal to the neural network 604 and provides a second signal to the PPG algorithm 606. In one scenario, the first signal and the second signal are different signals. This scenario includes the neural network 604 processing only a subset of all data available to the DSP 602, and these processed data are formatted to be simpler or more efficient for the neural network 604 to use, such as being normalized, or derivative of each other. Still keeping with this scenario, unlike the neural network 604, the PPG algorithm has access to all the data provided by the DSP 602, or at least more data than the subset processed by the neural network 604. The data provided by the DSP 602 to the PPG algorithm 606 in this scenario is unformatted data. Still keeping with this example, the neural network 604 provides a third signal to the photodiode control algorithm 608 and a fourth signal to the PPG algorithm 606, where the third signal is the same as the fourth signal, as the output of the neural network 604 is unique. Other embodiments may use a different neural network having more than one output, in which case the third signal and the fourth signal may be different.

The neural network 604 is, in at least one example, identical to the neural network 402. The neural network 604 is, in at least one example, identical to the neural network 502.

The photodiode control algorithm 608 uses two inputs to compute the bias voltage $V_{bias}$. First, if the PPG algorithm 606 detects that some peaks are wrongly detected or are missed, the PPG algorithm 606 may output a reliability signal to the photodiode control algorithm indicating a reliability (e.g., missed peak detection) of a heartbeat peak and provide that signal to the photodiode control algorithm 608 to improve signal quality by increasing the bias voltage $V_{bias}$. Second, by knowing where each peak is located based on the neural network 604, the photodiode control algorithm 608 can compare the peak's amplitude relative to the average signal value, as an indicator of signal quality. If signal quality is high, the bias voltage $V_{bias}$ can be decreased, and if it is low, it can be increased. In any case, how much the bias voltage $V_{bias}$ needs to be changed is computed by extrapolating the current signal quality to other bias voltages based on an understanding of how SNR varies with bias voltage $V_{bias}$.

In at least one example, the corresponding structure of the PPG algorithm 606 and the photodiode control algorithm 608, each separately or in combination, may include one or more microcontrollers, processors, or microprocessors and/or one or more memory devices such as DRAM, SRAM, flash memory, a magnetic disk drive, an optical drive, a PROM, a ROM, or any other memory and combination of memories. The one or more microcontrollers, processors, or microprocessors may implement algorithms, instructions, and/or programs that are stored on the one or more of the memory devices in order to perform the various processes of the present disclosure.

Figure 6B:
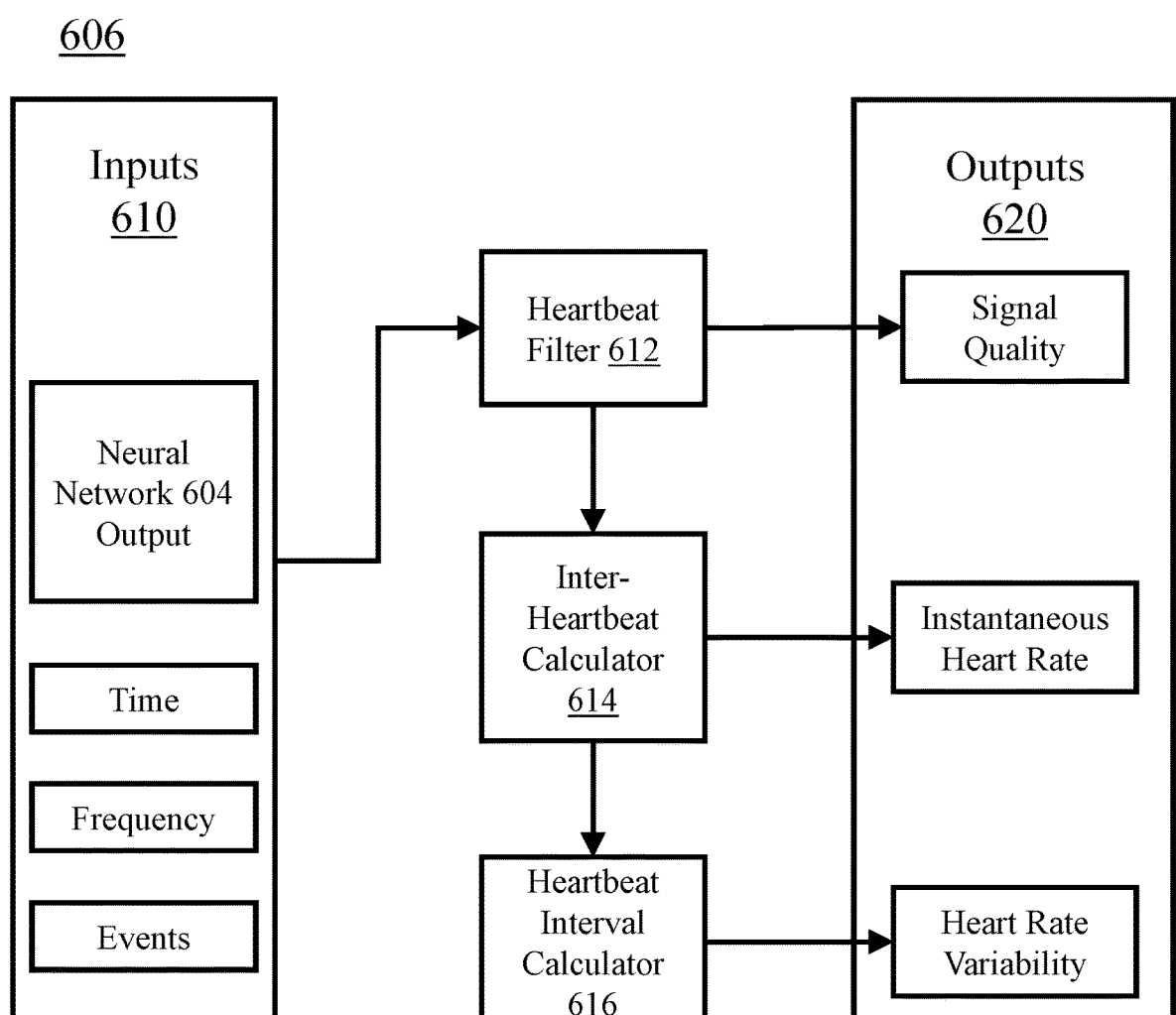
FIG. 6B shows a PPG algorithm for a neural network system, in accordance with an embodiment of the present disclosure.

FIG. 6B shows a detailed view of the PPG algorithm 606. The PPG algorithm 606, generally takes one or more inputs 610, processes those one or more inputs, and produces one or more outputs 620. In one example, the Health Data in FIG. 6A includes the outputs 620. It is to be understood that the PPG algorithm 606 is one example of a PPG algorithm applicable to the photodetectors, DPDs, and neural network systems described herein. Other PPG algorithms include more or fewer inputs, more or fewer outputs, and more or fewer intermediate processing steps between receiving the inputs 610 and producing the outputs 620.

The PPG algorithm 606 begins with receiving the one or more inputs 610. The inputs 610 include the output from the neural network 604 and one or more outputs of the DSP 602. The output of the neural network 604 includes, in at least one example, the health signal. The DSP 602 may output one or more of a value of time, a value of a frequency, or a copy of the signal supplied to the DSP 602. The inputs 610 may also include one or more events, which may be determined according to an applicable controller, sensors, and/or the neural network 604. In an example, an accelerometer and/or a gyroscope is used to detect that the photodetector has moved or has been removed entirely and therefore, the PPG algorithm 606 should not expect to acquire any useful data on the user's heartbeat. Other examples of events include the start or end of an exercising session, in which the heartrate could change rapidly.

The inputs 610 are provided to the heartbeat filter 612. The inputs 610 include, for example, the output of the neural network 604 indicating the presence of a heartbeat. The objective of the heartbeat filter 612 is to make sure that the heartbeat detected by the neural network 604 (i.e., a candidate heartbeat) is realistic or reliable, while avoiding false positives or negatives. If two heartbeats are too close to each other, then most likely one of them is a mistake from the neural network 604, and if the amount of time (i.e., delay) is too long between two heartbeats, then the signal has been lost (e.g., because the sensor was moved) or the neural network 604 is unable to detect the heartbeats because the signal has become poor. To determine if the amount of time corresponds to a reliable heartbeat detection, threshold values are established to determine what variation between heartbeats is tolerable. These thresholds can be fixed or can be adjusted using the user's heart rate profile (e.g., HRV, heart rate at rest). If the heartbeats satisfy the thresholds (i.e., are not too far apart or are too close), then a measure of signal quality may be included in the outputs 620.

A user's profile may indicate a range of values for any of the inputs 610 such that a controller may determine a heartbeat is valid if a measured value is within such a range. In an example, an event may correspond to an amount of motion within a particular range of motion or specified angles of rotation of a motion sensor (e.g., gyroscope).

Once a heartbeat is considered realistic or reliable, the PPG algorithm 606 computes the time interval between one heartbeat and the preceding heartbeat via the inter-heartbeat calculator 614 to output the instantaneous heart rate. Values of this instantaneous heart rate are shown above the PPG signal 802 in FIG. 8, which will be described later. Over a longer period of time, an average heartbeat may be calculated from the individual instantaneous heart rate values. The instantaneous heart rate may be included in the outputs 620. Another important metric of cardiovascular health besides heart rate is heart rate variability.

Heart Rate Variability (HRV) is a measure of the variation in time between each heartbeat. HRV is one of the best objective metrics for physical fitness as a high HRV generally may indicate that a person's body is responsive to both parasympathetic (deactivating) and sympathetic (activating) inputs of the nervous system and is ready to physically perform. A lower HRV, which usually means one of the inputs of the nervous system is dominating the other, may indicate a generally low level of fitness. These are generalized statements about HRV. However, HRV is very individualized, meaning it is a sensitive metric that fluctuates throughout the day, making HRV variability trends a point of focus for those monitoring their cardiovascular health. Thus, it may be more beneficial for a person to compare their own HRV trends to their prior data rather than comparing their HRV values to other people's HRV values.

Embodiments described herein are not limited to one particular HRV measurement definition or formula. In one example, the heartbeat interval calculator 616 receives the output of the inter-heartbeat calculator 614, computes the distribution of time intervals between consecutive heartbeats, and outputs the HRV as the standard deviation of this distribution. The HRV calculated by the heartbeat interval calculator 616 is included in the one or more outputs 620.

To optimize power consumption while acquiring PPG measurements, a controller (e.g., the controller 102) may utilize the output of the neural network 604, the signal quality output by the heartbeat filter 612, the instantaneous heart rate output by the inter-heartbeat calculator 614, and/or the HRV output by the heartbeat interval calculator 616. As previously discussed, there is a relationship between $N_{tot}$ and the bias voltage.

One objective in performing PPG measurements is reducing $N_{tot}$ as much as possible while still detecting heartbeats. In certain embodiments, this may be achieved without user data or data particular to other sensors that may acquire data about the user (e.g., accelerometer, gyroscope). However, the PPG algorithm 606, in certain embodiments, has access to previously measured heartbeats and heart rates. In these embodiments, a user profile, user data, accelerometer data, gyroscope data, and/or other data are utilized to improve convergence and event detection Each user will have produce different signal intensities, and the PPG algorithm 606 can adapt a personal voltage range for each user where PPG detection will work. Accelerometers and gyroscopes may be used for event detection, as signal quality tends to change when the sensor moves, and bias voltage $V_{bias}$ needs to be adjusted.

Figure 7:
FIG. 7 shows a dynamic photodiode's performance without a neural network system, in accordance with an embodiment of the present disclosure.

To demonstrate the significant power savings and performance improvements gained by the neural network systems disclosed herein, FIG. 7 shows a results screen 700 that includes a PPG signal 702. The PPG signal 702 is obtained using a DPD without any of the AI-based or neural network-based techniques described herein. Notably, the average power consumed by the DPD in obtaining the PPG signal 702 is 28.93 uW, the DPD triggering time is 262.72 us, and the bias voltage is 3.3 volts. After utilizing neural network systems as described herein, the results are vastly improved, as shown in FIG. 8.

Figure 8:
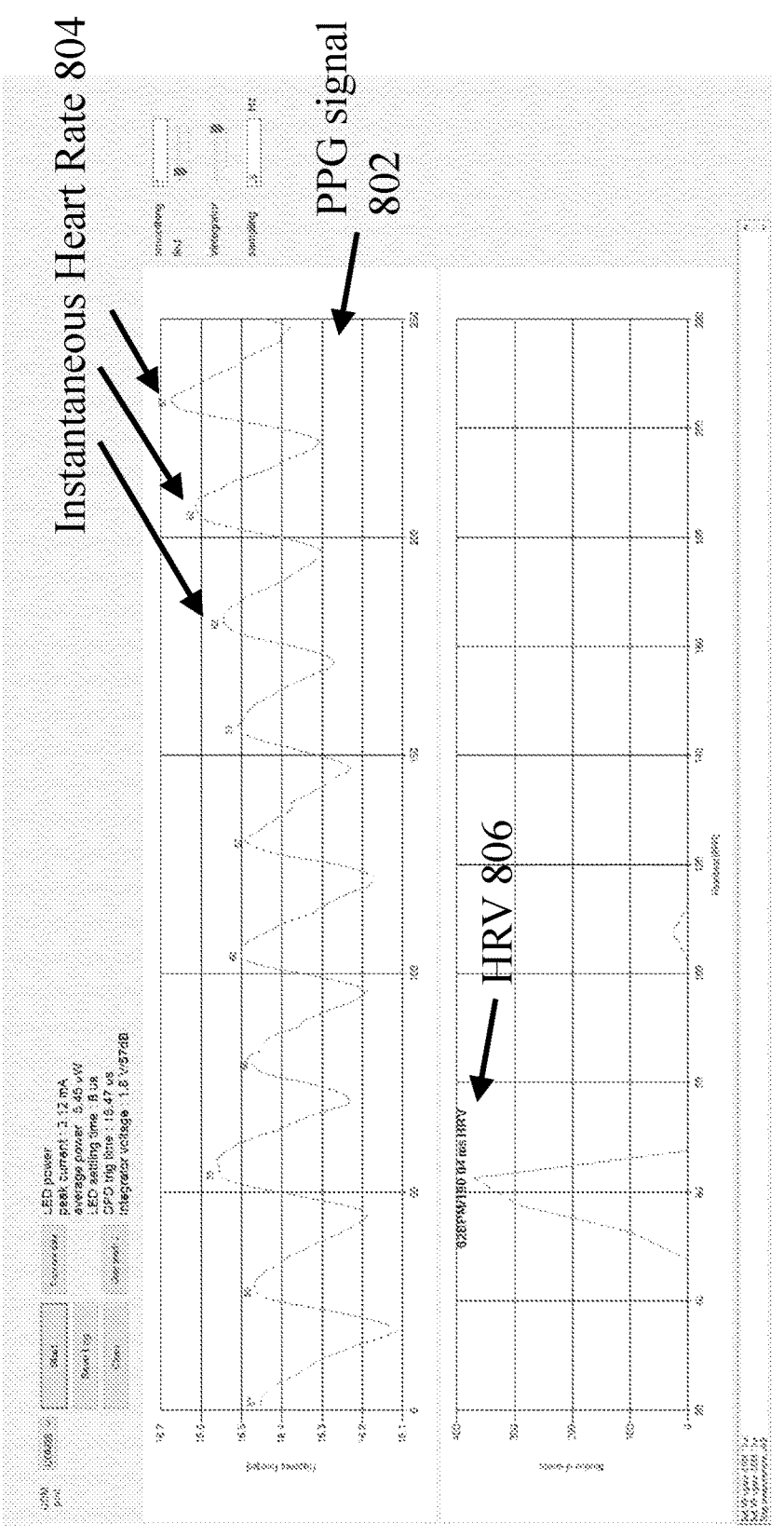
FIG. 8 shows a dynamic photodiode's performance with a neural network system, in accordance with an embodiment of the present disclosure.

FIG. 8 shows a results screen 800 that includes a PPG signal 802, instantaneous heart rate values 804, and an HRV 806. Beyond the additional functionalities of providing the instantaneous heart rate values 804 and the HRV 806, by utilizing the neural network systems described herein (e.g., the neural network system 500), the average power is reduced from 28.93 uW to 5.45 uW, the DPD triggering time is reduced from 262.72 us to 16.47 us, and the bias voltage is reduced from 3.3 volts to 1.8 volts. The "average power" described above includes DPD power and LED power. These results are one example of the many improvements gained by the embodiments described herein and other results are achievable that differ from those just described without departing from the benefits of the AI-based techniques herein described.

The present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

Notably, the photodetectors and DPDs of the present disclosure may be implemented as embedded devices fabricated with CMOS technology, as stand-alone devices using surface mount components, as part of a medical device (e.g., as a chip or circuit board included in a medical device having other sensors or electronic components), whether now known or later developed; all such configurations are intended to fall within the scope of the present disclosure. Further, any manufacturing technique, whether now known or later developed, may be employed to fabricate the photodetectors, DPDs, and neural network systems; all such techniques are intended to fall within the scope of the present disclosure.

At this point it should be noted that techniques for power minimization and photodetector measurement improvement in accordance with the present disclosure as described above may involve the processing of input data and the generation of output data to some extent. This input data processing and output data generation may be implemented in hardware or software. For example, specific electronic components may be employed in one or more processors, a dedicated circuit or similar or related circuitry for implementing the functions associated with taking PPG measurements with photodetectors, implementing PPG algorithms and photodiode control algorithms, implementing neural networks, performing event detection, and so forth in accordance with the present disclosure as described above. Alternatively, one or more processors operating in accordance with instructions may implement the functions associated with neural networks, controllers, algorithms, or other processes in accordance with the present disclosure as described above. If such is the case, it is within the scope of the present disclosure that such instructions may be stored on one or more non-transitory processor readable storage media (e.g., a magnetic disk, SSD or other storage medium), or transmitted to one or more processors via one or more signals embodied in one or more carrier waves.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A method for controlling a photodetector, the method comprising the steps of:
    receiving, by a system comprising memory and one or more processors, a target value of the photodetector;
    receiving, by the system, an output from the photodetector;
    processing, by a neural network of the system, the output from the photodetector;
    outputting, by the neural network, a health signal;
    generating, by the system and based at least on the health signal and the target value, a bias signal; and
    applying, by the system, the bias signal to the photodetector to drive the photodetector to the target value.

2. The method of claim 1, further comprising:

providing, by the system, the health signal to a photoplethysmography algorithm implemented by the system, wherein the photoplethysmography algorithm comprises:

determining from the health signal, a delay between a first candidate heartbeat and a second candidate heartbeat; and determining, a signal quality of the first candidate heartbeat and the second candidate heartbeat.

3. The method of claim 2, wherein determining the signal quality of the first candidate heartbeat and the second candidate heartbeat comprises:

determining that the health signal includes a false positive responsive to determining that a delay between the first candidate heartbeat and the second candidate heartbeat is lower than a first threshold amount of time; and/or determining that the health signal is unreliable responsive to determining that a delay between the first candidate heartbeat and the second candidate heartbeat is higher than a second threshold amount of time.

4. The method of claim 2, wherein the photoplethysmography algorithm further comprises:

computing an inter-beat interval between the first candidate heartbeat and the second candidate heartbeat.

5. The method of claim 4, wherein the photoplethysmography algorithm further comprises:

computing heart rate variability based on the inter-beat interval.

6. The method of claim 5, wherein computing heart rate variability comprises:

computing a distribution of inter-beat intervals, including the inter-beat interval; and computing the heart rate variability as a standard deviation of the distribution of inter-beat intervals.

7. The method of claim 2, further comprising:

receiving, by a digital signal processor of the system, data from one or more sensors;

providing, by the digital signal processor, a first signal to the neural network based on the data from the one or more sensors; and providing, by the digital signal processor, a second signal to the photoplethysmography algorithm based on the data from the one or more sensors, wherein the photoplethysmography algorithm determines the signal quality of the first candidate heartbeat and the second candidate heartbeat based on the health signal and the second signal.

8. The method of claim 1, further comprising:

determining, by the system, a reliability signal indicating a heartbeat peak is unreliable;

determining, by the neural network, a timing of the heartbeat peak; and providing, by the system, the reliability signal and the timing to a photodiode control algorithm implemented by the system, wherein the photodiode control algorithm comprises:

modifying the bias signal based on the reliability signal, the timing, and the target value.

9. The method of claim 8, wherein the bias signal is a bias voltage, and the photodiode control algorithm further comprises:

increasing the bias voltage responsive to determining the output from the photodetector has a signal quality below the target value; and/or lowering the bias voltage responsive to determining the output from the photodetector has a signal quality at or above the target value.

10. The method of claim 1, further comprising training the neural network, the neural network including an input layer, a hidden layer, and an output layer, the input layer including a plurality of parameters, the plurality of parameters including one or more of LED power, bias voltage, reflected power, background light, user data, data from an accelerometer, data from a gyroscope, and noise, wherein the output layer includes a node that corresponds to a detected heartbeat for a first logical value and corresponds to an absence of a detected heartbeat for a second logical value.

11. A system for controlling a photodetector, the system comprising:

one or more processors; and at least one memory, coupled to the one or more processors, and configured to provide the one or more processors with instructions that, when executed by the one or more processors, cause the system to:

receive a target value of the photodetector;

receive an output from the photodetector;

process, by a neural network of the system, the output from the photodetector;

output, by the neural network, a health signal;

generate, based at least on the health signal and the target value, a bias signal; and apply the bias signal to the photodetector to drive the photodetector to the target value.

12. The system of claim 11, wherein the instructions, when executed by the one or more processors, further cause the system to:

provide the health signal to a photoplethysmography algorithm implemented by the system, wherein the photoplethysmography algorithm causes the system to:

determine from the health signal, a delay between a first candidate heartbeat and a second candidate heartbeat; and determine a signal quality of the first candidate heartbeat and the second candidate heartbeat.

13. The system of claim 12, wherein determining the signal quality of the first candidate heartbeat and the second candidate heartbeat comprises:

determining that the health signal includes a false positive responsive to determining that a delay between the first candidate heartbeat and the second candidate heartbeat is lower than a first threshold amount of time; and/or determining that the health signal is unreliable responsive to determining that a delay between the first candidate heartbeat and the second candidate heartbeat is higher than a second threshold amount of time.

14. The system of claim 12, wherein the photoplethysmography algorithm further causes the system to compute an inter-beat interval between the first candidate heartbeat and the second candidate heartbeat.

15. The system of claim 14, wherein the photoplethysmography algorithm further causes the system to compute heart rate variability based on the inter-beat interval.

16. The system of claim 15, wherein compute heart rate variability based on the inter-beat interval comprises:

computing a distribution of inter-beat intervals, including the inter-beat interval; and computing the heart rate variability as a standard deviation of the distribution of inter-beat intervals.

17. The system of claim 12, wherein the instructions, when executed by the one or more processors, further cause the system to:

receive, by a digital signal processor of the system, data from one or more sensors;

provide, by the digital signal processor, a first signal to the neural network based on the data from the one or more sensors; and provide, by the digital signal processor, a second signal to the photoplethysmography algorithm based on the data from the one or more sensors, wherein the photoplethysmography algorithm causes the system to determine the signal quality of the first candidate heartbeat and the second candidate heartbeat based on the health signal and the second signal.

18. The system of claim 11, wherein the instructions, when executed by the one or more processors, further cause the system to:

determine a reliability signal indicating a heartbeat peak is unreliable;

determine, by the neural network, a timing of the heartbeat peak; and provide the reliability signal and the timing to a photodiode control algorithm implemented by the system, wherein the photodiode control algorithm causes the system to:

modify the bias signal based on the reliability signal, the timing, and the target value.

19. The system of claim 18, wherein the bias signal is a bias voltage, and the photodiode control algorithm further causes the system to:

increase the bias voltage responsive to determining the output from the photodetector has a signal quality below the target value; and/or lower the bias voltage responsive to determining the output from the photodetector has a signal quality at or above the target value.

20. One or more non-transitory computer-readable media storing executable instructions that, when executed by one or more processors, cause a system to control a photodetector by:

receiving a target value of the photodetector;

receiving an output from the photodetector;

processing, by a neural network of the system, the output from the photodetector;

outputting, by the neural network, a health signal;

generating, based at least on the health signal and the target value, a bias signal; and applying the bias signal to the photodetector to drive the photodetector to the target value.

* * * * *